(12) United States Patent
Cramer et al.

(10) Patent No.: US 10,583,429 B2
(45) Date of Patent: Mar. 10, 2020

(54) MIXED MODE LIGANDS

(71) Applicants: Bio-Rad Laboratories, Inc., Hercules, CA (US); Rensselaer Polytechnic Institute, Troy, NY (US)

(72) Inventors: Steven Cramer, Niskayuna, NY (US); James Woo, Troy, NY (US); Hong Chen, San Ramon, CA (US); Jiali Liao, San Ramon, CA (US); Russell Frost, Concord, CA (US)

(73) Assignees: Bio-Rad Laboratories, Inc., Hercules, CA (US); Rensselaer Polytechnic Institute, Troy, NY (US)

( * ) Notice: Subject to any disclaimer, the term of this patent is extended or adjusted under 35 U.S.C. 154(b) by 563 days.

(21) Appl. No.: 14/657,701

(22) Filed: Mar. 13, 2015

(65) Prior Publication Data

US 2015/0258539 A1 Sep. 17, 2015

Related U.S. Application Data

(60) Provisional application No. 61/953,365, filed on Mar. 14, 2014.

(51) Int. Cl.
*B01J 39/26* (2006.01)
*B01J 39/20* (2006.01)
(Continued)

(52) U.S. Cl.
CPC ......... *B01J 39/20* (2013.01); *B01J 20/28004* (2013.01); *B01J 20/286* (2013.01);
(Continued)

(58) Field of Classification Search
None
See application file for complete search history.

(56) References Cited

U.S. PATENT DOCUMENTS

| 4,452,931 A | 6/1984 | Okamoto et al. |
| 5,645,717 A | 7/1997 | Hjértén et al. |

(Continued)

FOREIGN PATENT DOCUMENTS

| CN | 1898265 | 1/2007 |
| CN | 1972746 | 5/2007 |

(Continued)

OTHER PUBLICATIONS

"UNOsphere™ Q & S Ion Exchange Media—Instruction Manual"; Bio-Rad Laboratories, Inc. Sep. 17, 2001. 5 pages.
(Continued)

*Primary Examiner* — Kara M Peo
(74) *Attorney, Agent, or Firm* — Kilpatrick Townsend & Stockton LLP

(57) ABSTRACT

The present disclosure is directed to mixed mode chromatography media comprising a ligand directly attached to a solid support. In some aspects, the ligand has a chemical formula of (Continued)

The mixed mode chromatography media is useful for binding and purifying proteins from a solution.

7 Claims, 12 Drawing Sheets

(51) Int. Cl.
*C07K 1/16* (2006.01)
*B01J 20/286* (2006.01)
*B01J 20/32* (2006.01)
*B01J 20/28* (2006.01)

(52) U.S. Cl.
CPC ....... *B01J 20/28085* (2013.01); *B01J 20/321* (2013.01); *B01J 20/3253* (2013.01); *B01J 20/3285* (2013.01); *B01J 39/26* (2013.01); *C07K 1/165* (2013.01); *B01J 2220/82* (2013.01)

(56) References Cited

U.S. PATENT DOCUMENTS

| | | | |
|---|---|---|---|
| 5,647,979 | A | 7/1997 | Liao et al. |
| 5,935,429 | A | 8/1999 | Liao et al. |
| 5,945,520 | A | 8/1999 | Burton et al. |
| 6,423,666 | B1 | 7/2002 | Liao et al. |
| 6,498,236 | B1 | 12/2002 | Lihme et al. |
| 6,919,436 | B2 | 7/2005 | Lihme et al. |
| 8,114,280 | B2 | 2/2012 | Maloisel et al. |
| 8,188,242 | B2 * | 5/2012 | Gagnon ........... A61K 39/39591 424/176.1 |
| 8,236,800 | B2 * | 8/2012 | DeGrado ............... A61K 31/16 514/247 |
| 8,685,248 | B2 | 4/2014 | Glad et al. |
| 2005/0020812 | A1 | 1/2005 | Angus |
| 2007/0244307 | A1 | 10/2007 | Engstrand et al. |
| 2008/0132683 | A1 | 6/2008 | Lihme et al. |
| 2009/0270596 | A1 | 10/2009 | Gagnon et al. |
| 2013/0102761 | A1 | 4/2013 | Liao et al. |

FOREIGN PATENT DOCUMENTS

| | | |
|---|---|---|
| WO | 2009/126603 A1 | 10/2009 |
| WO | 2011/012722 A1 | 2/2011 |
| WO | 2011/049798 A1 | 4/2011 |

OTHER PUBLICATIONS

Extended European Search Report from EP Appl. No. 12841318.3, dated May 29, 2015.
International Search Report and Written Opinion from International Application No. PCT/US2012/061154, dated Mar. 5, 2013.
Partial Search Report for International Application No. PCT/US2015/020484, dated May 19, 2015 (2 pages).
General Electric. "Capto MMC", Announcement GE Healthcare No. 11-0035-45AA, Jan. 1, 2005.
Life Technologies. POROS HS 50 um Bulk Media. 2014.
Pubchem. Substance Summary for: SID 210323253. Deposit Date: Oct. 11, 2014. [retrieved on Jul. 2015]. Retrieved from the Internet at URL at: https:/lpubchem.ncbi.nlm.nih.gov /summary /summary.cgi?from=substance&sid=210323253>.
International Search Report and Written Opinion from Application No. PCT/US2015/020484, dated Sep. 2, 2015.

* cited by examiner

MIXED MODE LIGANDS

CROSS-REFERENCE TO RELATED PATENT APPLICATIONS

The present patent application claims benefit of priority to U.S. Provisional Patent Application No. 61/953,365, filed Mar. 14, 2014, which is incorporated by reference for all purposes.

There is a written joint research agreement in the field of the invention between Bio-Rad Laboratories and Rensselaer Polytechnic Institute.

BACKGROUND OF THE INVENTION

The extraction of immunoglobulins and other proteins from source liquids, which are primarily mammalian bodily fluids or cell culture harvest, is of value in obtaining the proteins in a sufficiently concentrated or purified form for diagnostic and therapeutic uses as well as laboratory studies in general. Purifications of native or recombinant proteins, and particularly immunoglobulins, often suffer however from such factors as low yield, the use of costly separation media, the leaching of separation media into the product, and concerns for the safe disposal of extraneous materials used in the extraction process.

BRIEF SUMMARY OF THE INVENTION

In some embodiments, a method of purifying a target protein from a source solution is provided. In some embodiments, the method comprises contacting a solid support linked to a ligand, wherein the ligand is:

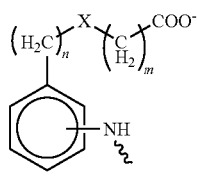

Formula I wherein n is 0, 1, or 2; m is 1, 2, 3, or 4; X is selected from S, C(O)—NH, NH—C(O), C(O)—NH—CH$_2$—C(O)—NH, or SO$_2$, and the amine can be at the para, ortho or meta position on the benzyl ring;
or

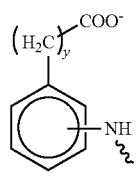

Formula II wherein y is 1, 2, 3, 4, or 5 and the amine can be at the para, ortho or meta position on the benzyl ring,
thereby binding the target protein to the ligand; and eluting the target protein, thereby purifying the target protein.

In some embodiments, the ligand of Formula I is selected from the group consisting of

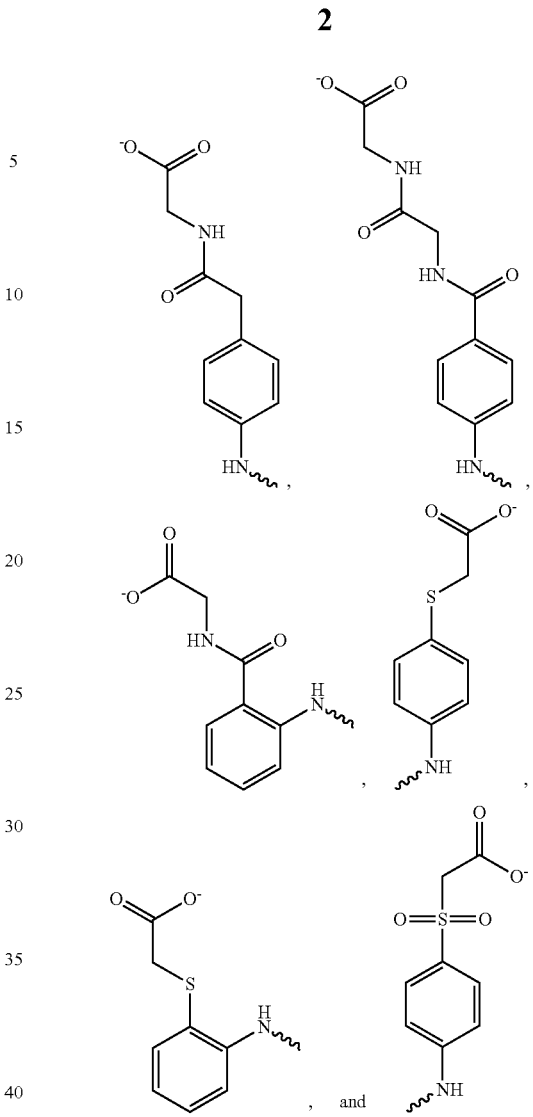

, and

.

In some embodiments, the ligand of Formula II is selected from the group consisting of

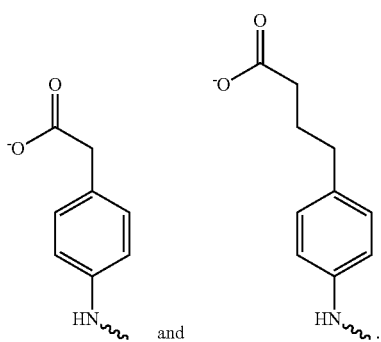

and

.

In some embodiments, the solid support has pores of a median diameter of 0.5 micron or greater, optionally with substantially no pores of 0.1 micron or less in diameter. In some embodiments, the solid support consists of particles having a median particle size of from about 25 microns to about 150 microns.

In some embodiments, the contacting is performed at a pH of about 4.0 to about 6.0 and eluting is performed at a pH of from about 6.1 to about 8.5

In some embodiments, the solid support is a membrane. In some embodiments, the solid support is a monolith.

In some embodiments, the source solution contains a salt selected from alkali metal and alkaline earth metal halides at a concentration of from about 50 mM to about 300 mM. In some embodiments, the source solution contains a salt selected from alkali metal and alkaline earth metal halides at a concentration of from about 100 mM to about 150 mM.

Also provided is a mixed-mode chromatography medium comprising a ligand coupled to a solid support, wherein the ligand selected from Formula I or Formula II. In some embodiments, the medium is in contact with a source solution under conditions such that a protein target in from the source solution binds to the ligand.

In some embodiments, the ligand of Formula I is selected from the group consisting of

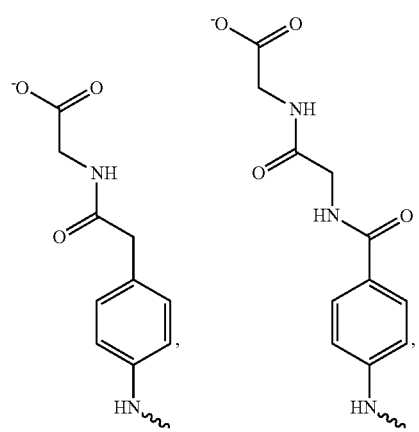

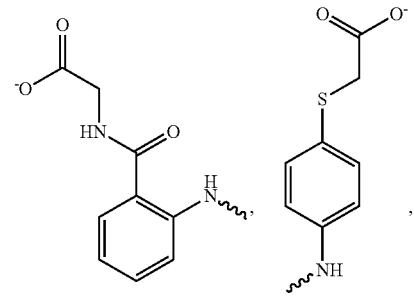

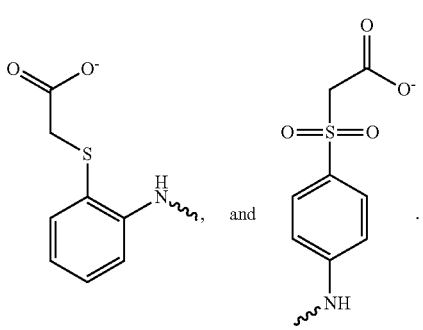

In some embodiments, the ligand of Formula II is selected from the group consisting of

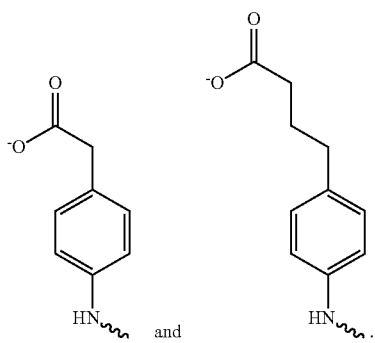

In some embodiments, the solid support has pores of a median diameter of 0.5 micron or greater with substantially no pores of 0.1 micron or less in diameter. In some embodiments, the solid support consists of particles having a median particle size of from about 25 microns to about 150 microns.

In some embodiments, the solid support is a membrane. In some embodiments, the solid support is a monolith.

DETAILED DESCRIPTION OF THE INVENTION

I. Introduction

Figure 1:
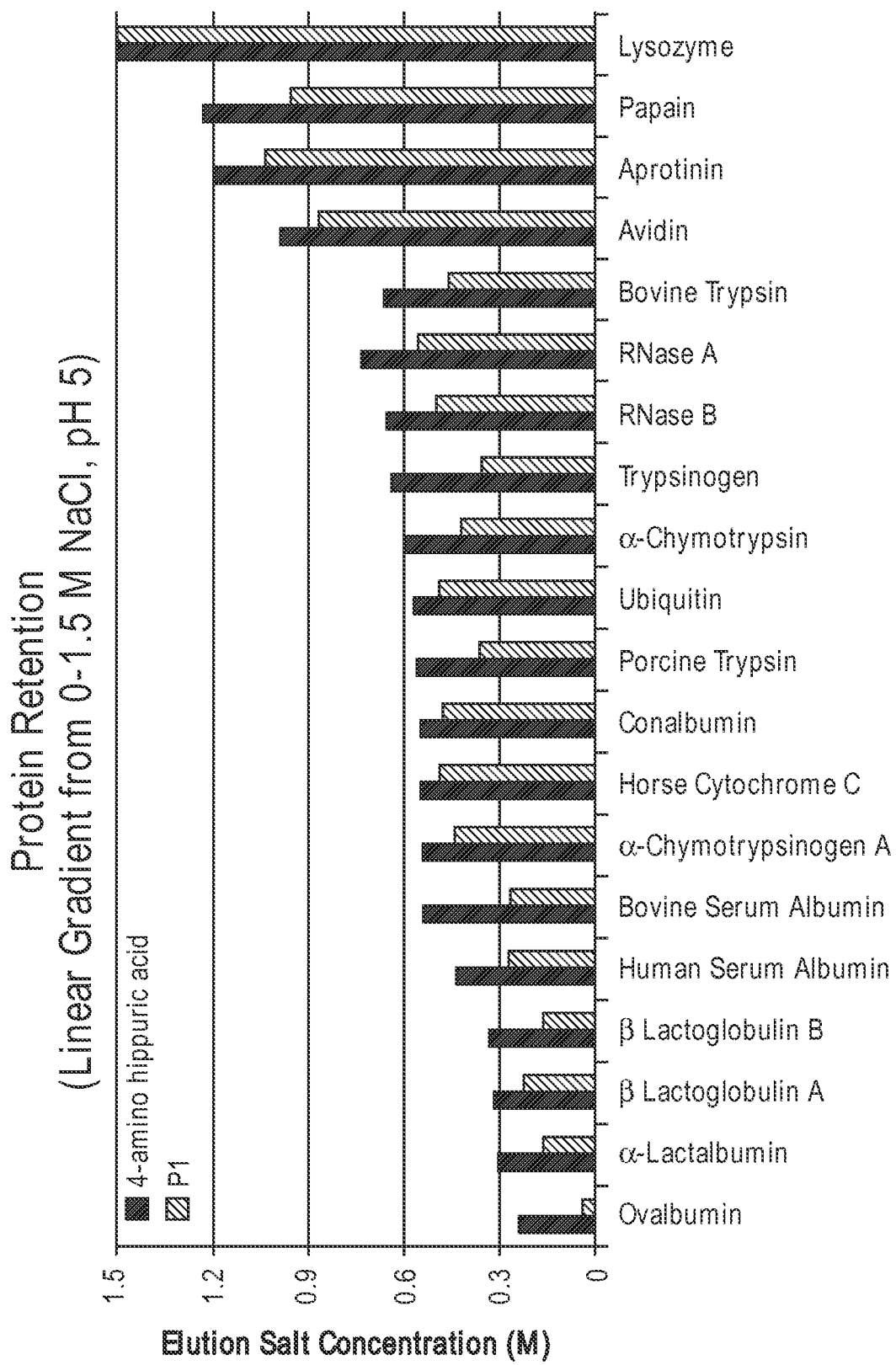
FIGS. 1-12 display the concentration of sodium chloride in a linear gradient at which bound protein is eluted from the solid support. The protein tested is listed in the horizontal axis. The order from top to bottom of ligands listed in the upper left corner corresponds to the data for each protein listed from left to right.
Figure 2:
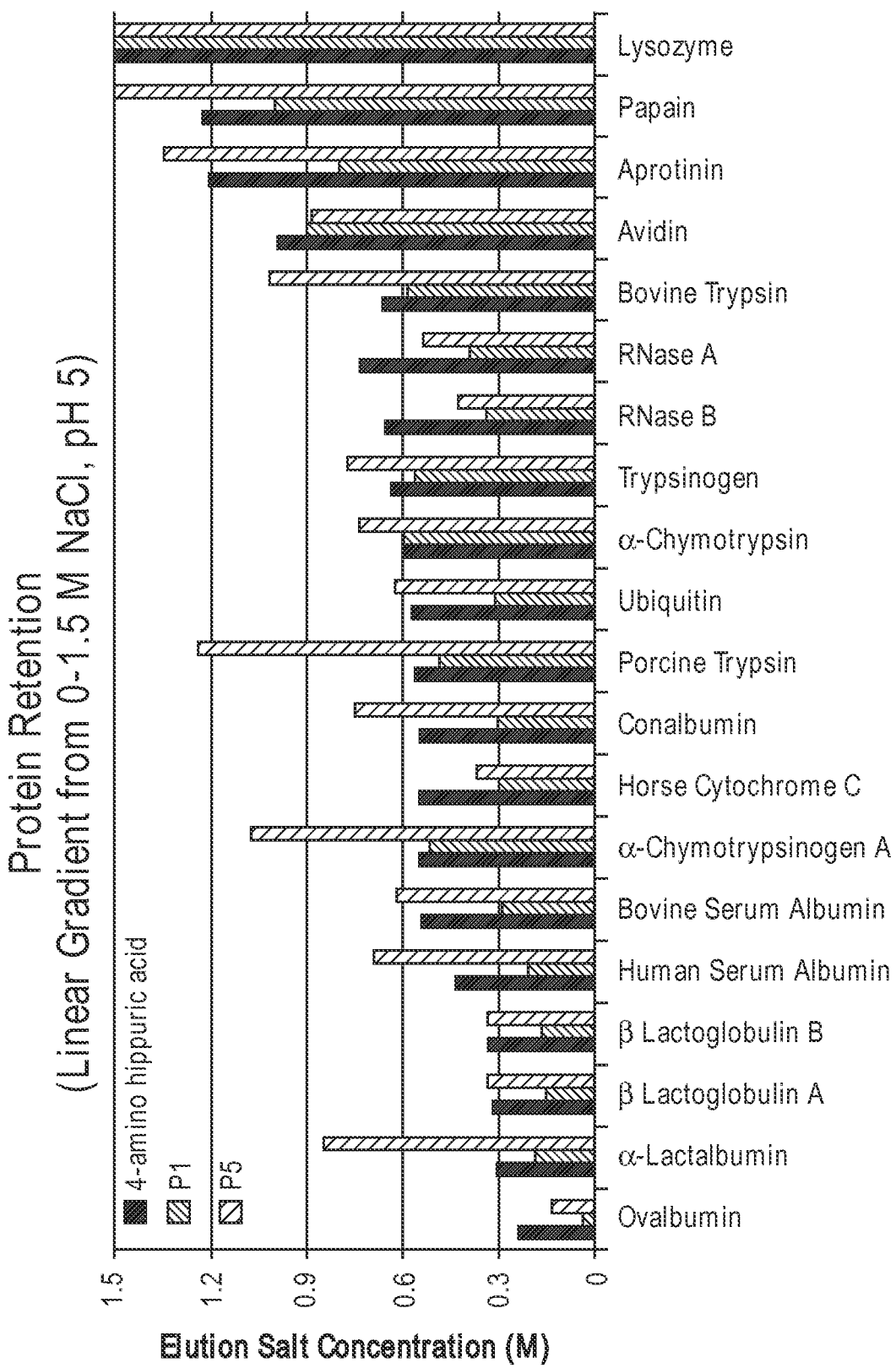
Figure 3:
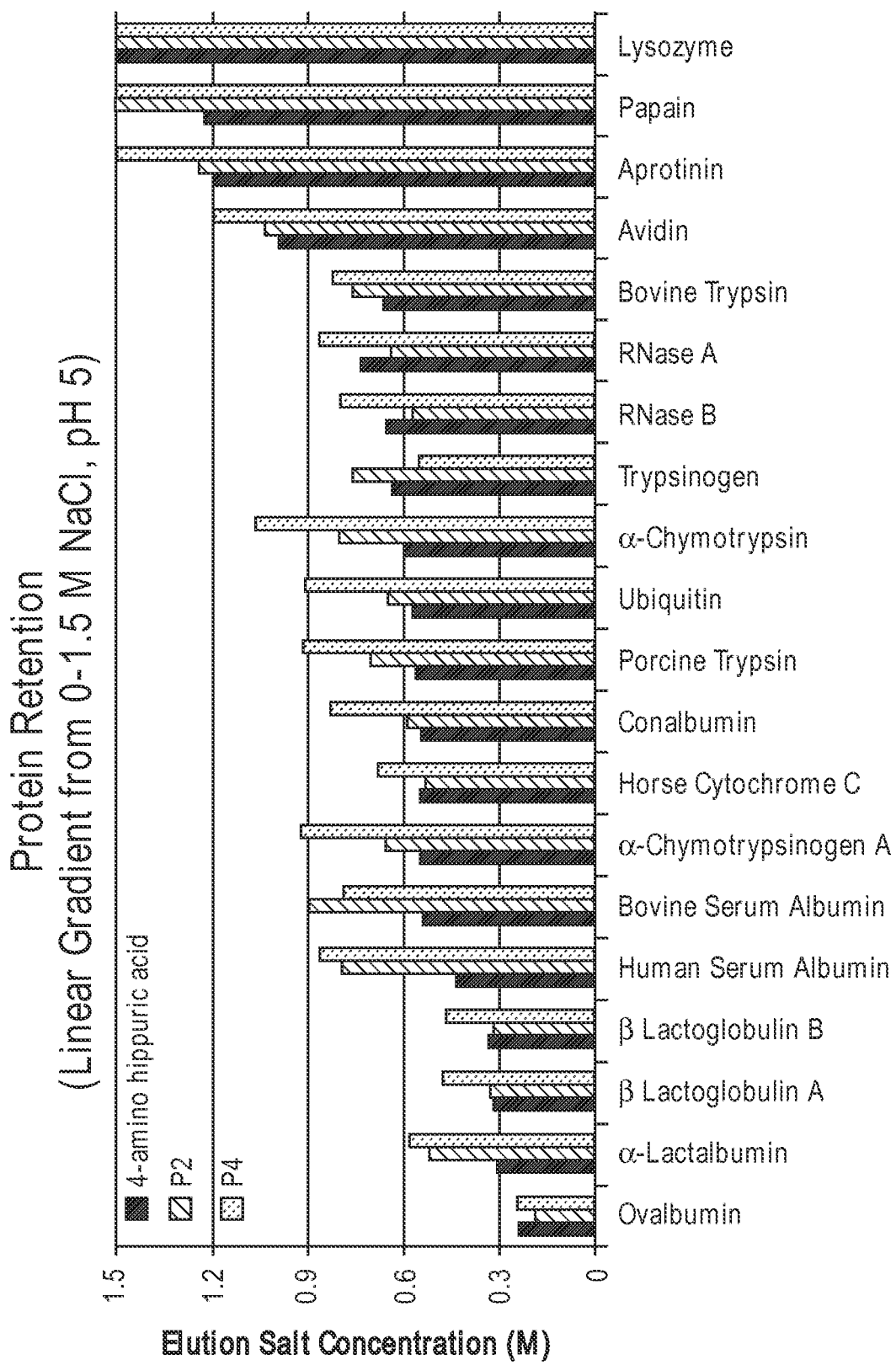
Figure 4:
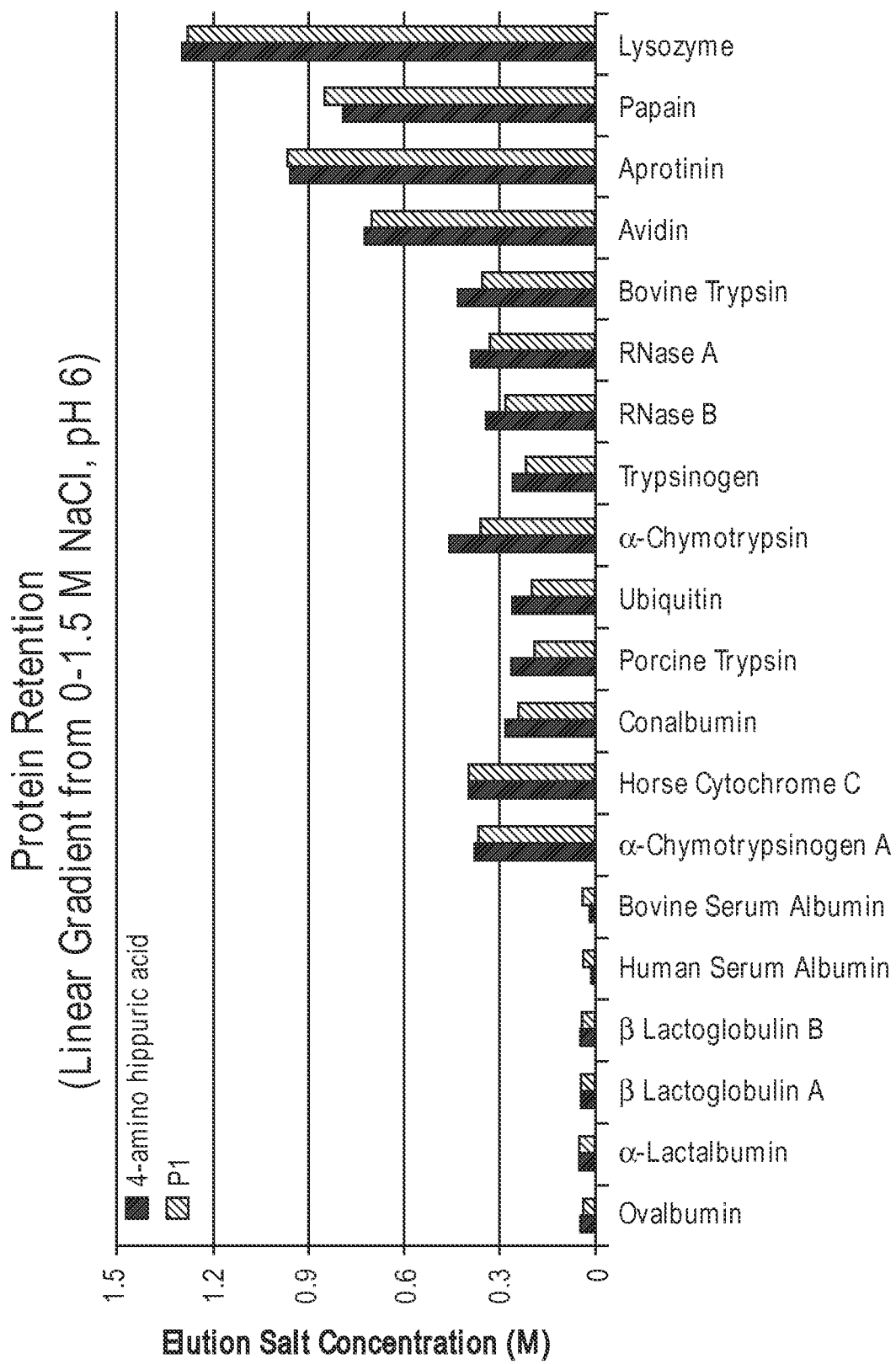
Figure 5:
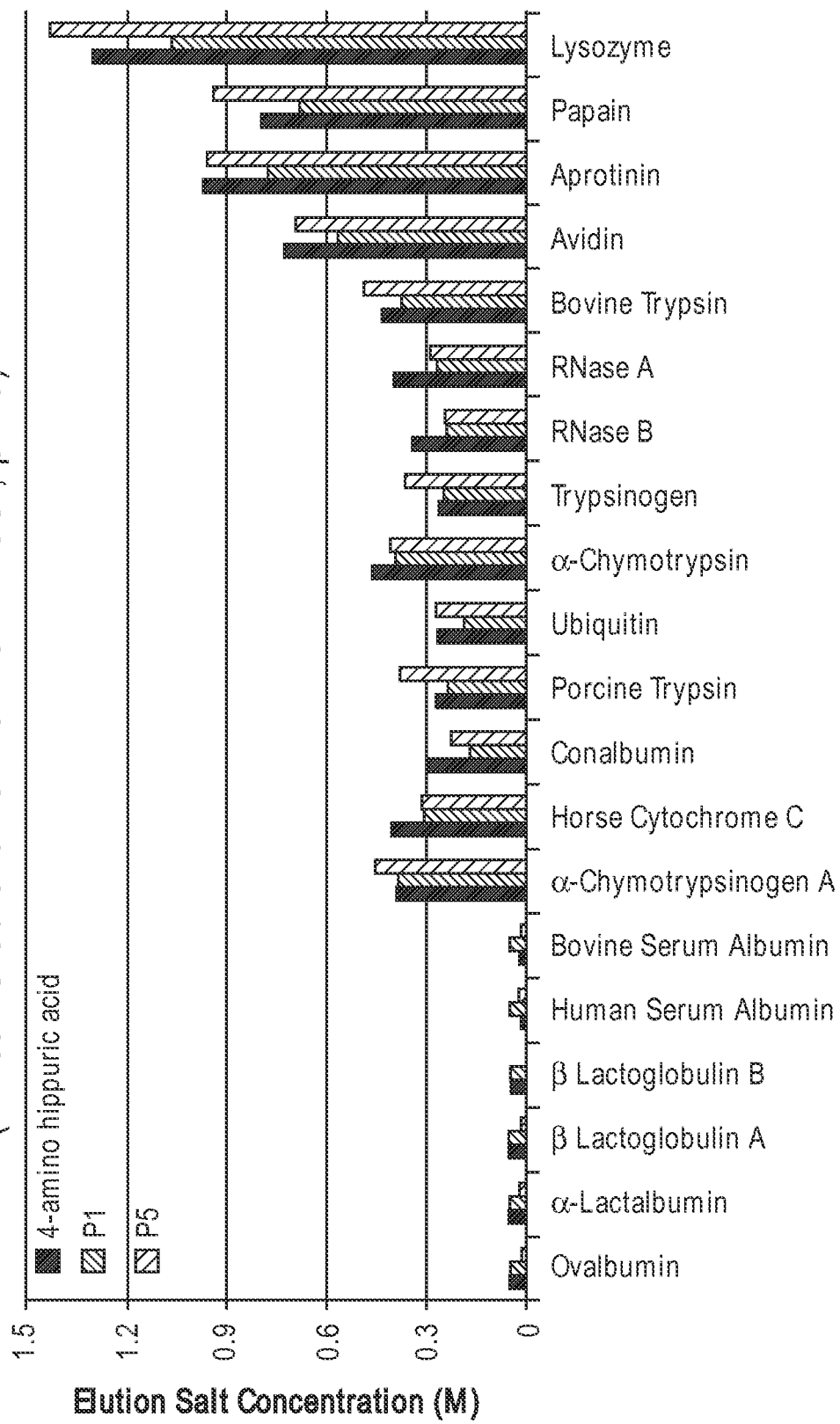
Figure 6:
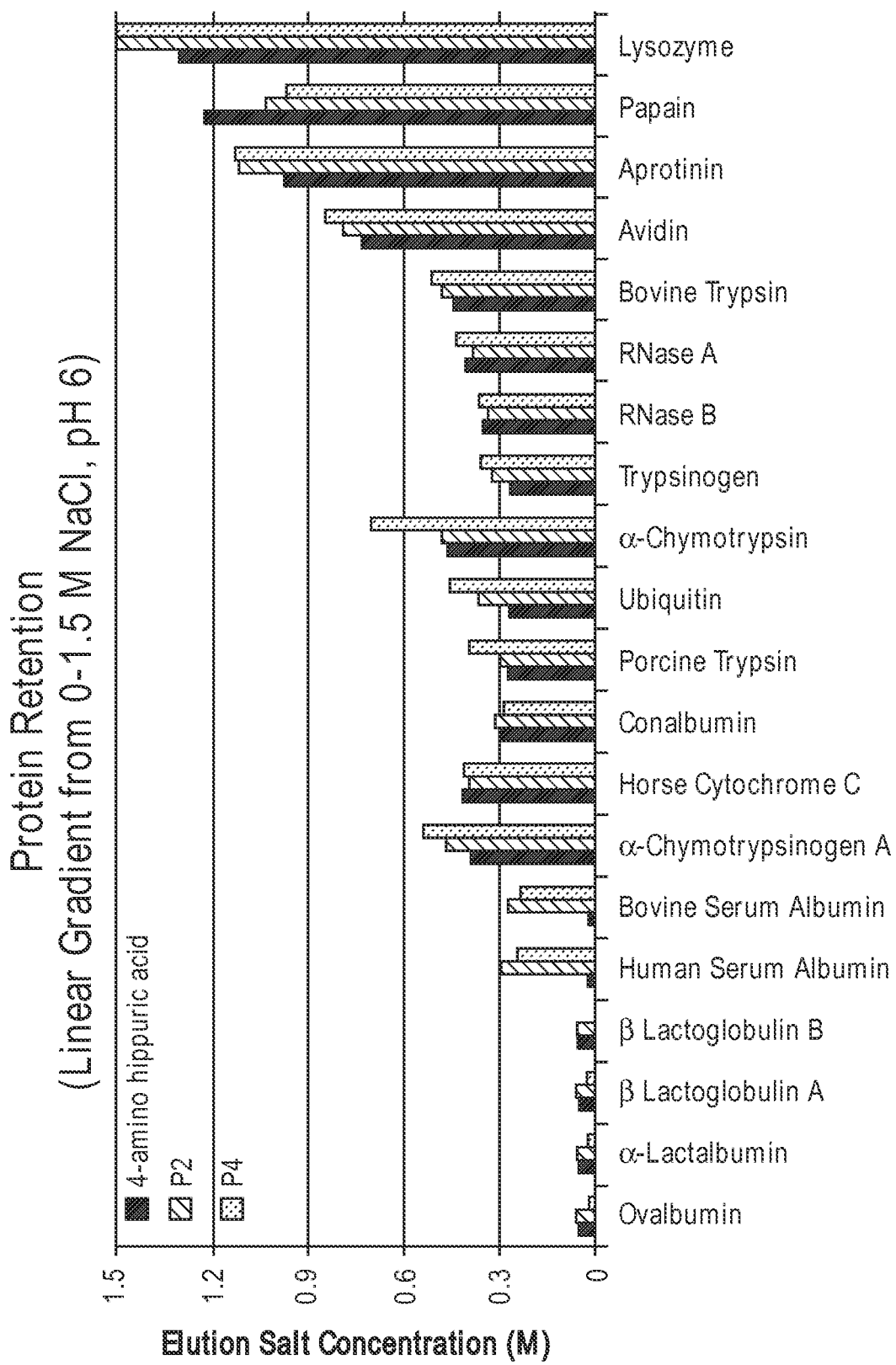

New protein binding specificities and binding strengths were discovered for a variety of mixed mode ligands having a hydrophobic and an anionic (cation exchange) moiety. Accordingly, chromatography solid supports linked to the mixed mode ligands described herein, as well as methods for purifying proteins with the mixed mode ligands, are provided.

II. Ligands

Ligands for protein purification can be selected from Formulas I and II:

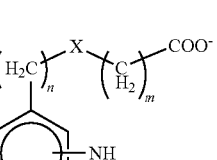

Formula I

In some embodiments, n is 0, 1, or 2; m is 1, 2, 3, or 4; X is selected from S, C(O)—NH, NH—C(O), C(O)—NH—CH$_2$—C(O)—NH, or SO$_2$, and the amine can be at the para, ortho or meta position on the benzyl ring. In some embodiments, n is 0, 1, or 2; m is 1, 2, 3, or 4; X is selected from S, C(O)—NH, NH—C(O), C(O)—NH—CH$_2$—C(O)—NH, or $SO_2$, and the amine can be at the ortho or meta position on the benzyl ring. In some embodiments, n is 0, 1, or 2; m is 1, 2, 3, or 4; X is selected from S, NH—C(O), C(O)—NH—$CH_2$—C(O)—NH, or $SO_2$, and the amine can be at the para, ortho or meta position on the benzyl ring. In some embodiments, n is 0, 1, or 2; m is 2, 3, or 4; X is selected from S, C(O)—NH, NH—C(O), C(O)—NH—$CH_2$—C(O)—NH, or $SO_2$, and the amine can be at the para, ortho or meta position on the benzyl ring. In some embodiments, n is 1, or 2; m is 1, 2, 3, or 4; X is selected from S, C(O)—NH, NH—C(O), C(O)—NH—$CH_2$—C(O)—NH, or $SO_2$, and the amine can be at the para, ortho or meta position on the benzyl ring.

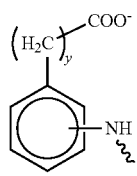

Formula II

In some embodiments, y is 1, 2, 3, 4, or 5. In Formula I, the amine can be at the para, ortho or meta position on the benzyl ring.

In all structures provided herein, the curving line from the amine indicates where the ligand is attached to the solid matrix (also referred to herein as a solid support), with or without an intermediate linking group.

In some embodiments, the ligands of Formula I are selected from the following:

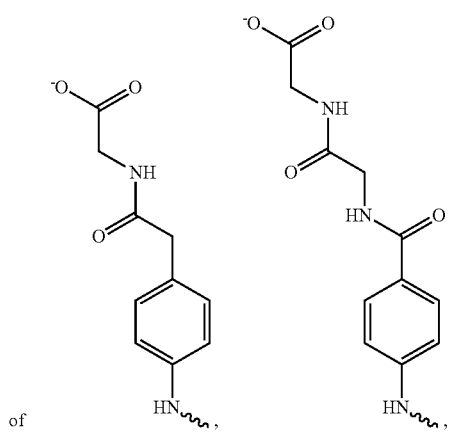

of

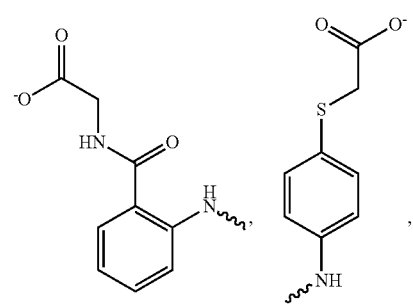

-continued

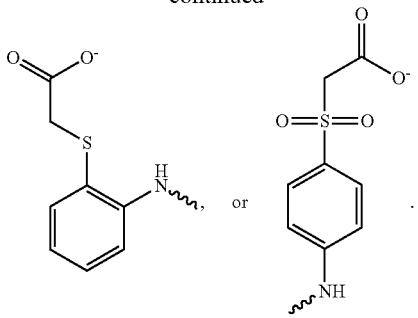

In some embodiments, the ligands of Formula II as selected from the following:

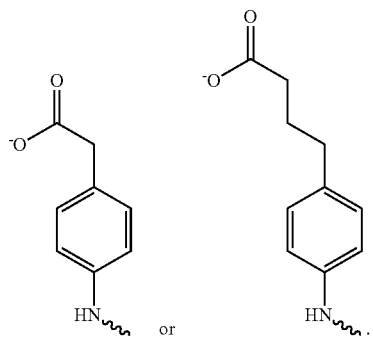

Any solid support is contemplated for linkage to the ligands. The solid support can be, for example, porous or non-porous and can be in the form, for example, of a matrix, bead, particle, chip, or other conformation, e.g., a membrane or a monolith, i.e., a single block, pellet, or slab of material. Particles when used as matrices can be spheres or beads, either smooth-surfaced or with a rough or textured surface. Many, and in some cases all, of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is in some embodiments within the range of about 25 microns to about 150 microns. Disclosures of matrices meeting the descriptions in this paragraph and the processes by which they are made are found in Hjertén et al., U.S. Pat. No. 5,645,717, Liao et al., U.S. Pat. No. 5,647,979, Liao et al., U.S. Pat. No. 5,935,429, and Liao et al., U.S. Pat. No. 6,423,666. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases.

The ligands can be linked directly (without a spacer) to the solid support or via a linker. Linkage to the solid support will depend on the specific solid support used. In some embodiments, the solid support comprises a diol, which is converted to an aldehyde, e.g., by conversion with $NaIO_4$. The amine of the ligand can be linked to an aldehyde on the solid support by a reductive amination reaction, thereby directly coupling the ligand to the solid support.

In some embodiments, the ligand is linked to the solid support via a spacer. The spacer may be introduced according to conventional covalent coupling methodologies. Exemplary coupling chemistries can involve, for example, epichlorohydrin, epibromohydrin, allyl-glycidylether, bisepoxides such as butanedioldiglycidylether, halogen-substituted aliphatic substances such as di-chloro-propanol, divinyl sulfone, carbonyldiimidazole, aldehydes such as glutaric dialdehyde, quinones, cyanogen bromide, periodates such as sodium-meta periodate, carbodiimides, chloro-triazines, sulfonyl chlorides such as tosyl chlorides and tresyl chlorides, N-hydroxy succinimides, oxazolones, maleimides, 2-fluoro-1-methylpyridinium toluene-4-sulfonates, pyridyl disulfides and hydrazides.

In some embodiments, the support matrix is one with pores of a median diameter of 0.5 micron or greater, with substantially no pores of less than 0.1 micron in diameter. In certain embodiments, the median pore diameter ranges from about 0.5 micron to about 2.0 microns. The pore volume can vary. In some embodiments, the pore volume will range from about 0.5 to about 2.0 cc/g. The matrix can be particles, a membrane or a monolith, and by "monolith" is meant a single block, pellet, or slab of material. Particles when used as matrices can be spheres or beads, either smooth-surfaced or with a rough or textured surface. Many, and in some cases all, of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is preferably within the range of about 25 microns to about 150 microns. Disclosures of matrices meeting the descriptions in this paragraph and the processes by which they are made are found in Hjertén et al., U.S. Pat. No. 5,645,717, Liao et al., U.S. Pat. No. 5,647,979, Liao et al., U.S. Pat. No. 5,935,429, and Liao et al., U.S. Pat. No. 6,423,666. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases. Cross-linking agents are also of use in many embodiments, and when present will generally constitute a mole ratio of from about 0.1 to about 0.7 relative to total monomer. Examples of crosslinking agents are dihydroxyethylenebisacrylamide, diallyltartardiamide, triallyl citric triamide, ethylene diacrylate, bisacrylylcystamine, N,N'-methylenebisacrylamide, and piperazine diacrylamide.

For purposes of the formation of a linkage with the ligand, and particularly ligands with amine groups, the inclusion of monomers with vicinal diols can be useful. One example is allyloxy propandiol (3-allyloxy-1,2-propanediol). Vicinal diol monomers can be used with other monomers to prepare copolymers. The diol group density in the polymers produced from diol-containing monomers can vary widely, such as for example densities within a range of from about 100 to 1,000 µmol/mL (i.e., micromoles of diol per milliliter of packed beads), and in many cases a range of from about 200 to 300 µmol/mL. An example of a matrix that meets this description and is commercially available is UNOsphere™ Diol (Bio-Rad Laboratories, Inc., Hercules, Calif., USA). To couple a pendant amine-containing ligand to a matrix with exposed vicinal diols, the diols can be oxidized to aldehyde groups, and the aldehyde groups can then be coupled to amine groups to form secondary amino linkages, all by conventional chemistry techniques well known in the art.

Protein purification utilizing a resin (i.e., separation medium) as described herein can be achieved by conventional means known to those of skill in the art. Examples of proteins include but are not limited to antibodies, enzymes, growth regulators, clotting factors, transcription factors and phosphoproteins. In many such conventional procedures, the resin prior to use is equilibrated with a buffer at the pH that will be used for the binding of the target protein (e.g., antibody or non-antibody protein). Equilibration can be done with respect to all features that will affect the binding environment, including ionic strength and conductivity when appropriate.

In some embodiments, the resins described herein can be used in "bind-elute" mode to purify a target protein from a biological sample. "Bind-elute mode" refers to an operational approach to chromatography in which the buffer conditions are established so that target molecules and, optionally undesired contaminants, bind to the ligand when the sample is applied to the ligand (which is optionally bound to a solid support). Fractionation of the target can be achieved subsequently by changing the conditions such that the target is eluted from the support. In some embodiments, contaminants remain bound following target elution. In some embodiments, contaminants either flow-through or are bound and eluted before elution of the target. In some embodiments, following binding of the target protein to the resin, a change in pH or increase in salt concentration can be used to elute the target protein.

In some embodiments, once the resin is equilibrated, the source liquid is loaded onto the resin while maintaining the source liquid, and any additional carrier liquid when used, to a pH below 6.0 with an appropriate buffer, allowing the target protein to bind to the resin. In some embodiments, solutions having salt concentrations in the range of salt concentrations of cell cultures (e.g., 50-300 mM, or about 100-150 mM) are used. Thus, in some embodiments, the protein is loaded to the resin under such salt concentrations.

In some embodiments, the resin is then washed with a wash liquid, optionally at the same pH as that of the loading step, to remove any unbound biological species that may have been present in the source liquid.

The bound protein (e.g., antibody or non-antibody protein, as desired) can be subsequently eluted. In some embodiments, the protein is then eluted with an elution liquid at a pH above 6.0. Illustrative pH ranges, as cited above, are pH 4.0-6.0 for the binding and washing steps, and pH 6.1-8.5 for the elution step. In certain embodiments, the binding and washing steps are performed with the inclusion of a salt in the sample and wash liquids. Examples of salts that can be used for this purpose are alkali metal and alkaline earth metal halides, notably sodium and potassium halides, and as a specific example sodium chloride. The concentration of the salt can vary; in most cases, an appropriate concentration will be one within the range of about 10 mM to about 1M. As will be seen in the working examples below, optimal elution conditions for some proteins will involve a buffer with a higher salt concentration than that of the binding buffer, and in other cases by a buffer with a lower salt concentration than that of the binding buffer. The optimal choice in any particular case is readily determined by routine experimentation.

The resin can be utilized in any conventional configuration, including packed columns and fluidized or expanded-bed columns, and by any conventional method, including batchwise modes for loading, washes, and elution, as well as continuous or flow-through modes. The use of a packed flow-through column is particularly convenient, both for preparative-scale extractions and analytical-scale extractions. In some embodiments, the column ranges in diameter from 1 cm to 1 m, and in height from 1 cm to 30 cm or more.

"Antibody" refers to an immunoglobulin, composite (e.g., fusion), or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

Any antibody preparation can be used in the present invention, including unpurified or partially purified antibodies from natural, synthetic, or recombinant sources. Unpurified antibody preparations can come from various sources including, but not limited to, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination of the foregoing. In some embodiments, the antibodies have not been purified by protein A affinity prior to purification.

As noted above, the resins are also useful for purification of non-antibody proteins. Examples of therapeutic proteins include, but are not limited to, Factor VIII von Willebrand Factor enzymes, growth regulators, clotting factors, transcription factors and phosphoproteins.

EXAMPLES

A variety of possible ligands (see Table 1) for mixed mode chromatography were obtained from commercial sources (or in the case of ligand P4 and P9, below, synthesized) and linked to the solid support UNOsphere™ Diol, a copolymer of 3-allyloxy-1,2-propanediol and vinyl pyrrolidinone.

TABLE 1

| ligand | Structure | Vendor | Designation in figures |
|---|---|---|---|
| 2-(4-aminobenzamido) ethanesulfonate | 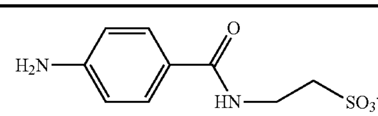 | Hande Sciences | P1 CAS 860707-78-4 |
| 4-aminophenylthioacetic acid | 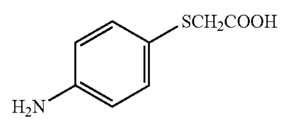 | Alfa Aesar | P2 CAS 104-18-7 |
| 4-aminophenylacetic acid | 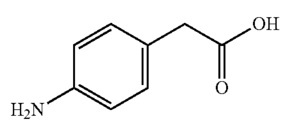 | Alfa Aesar | P3 CAS 1197-55-3 |
| 2-aminohippuric acid HCl or Abz-Gly-OH HCl | 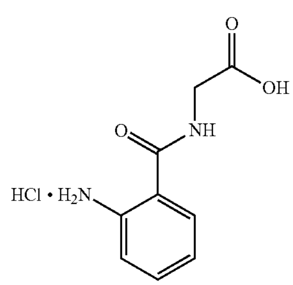 | BOC Sciences, Creative Dynamics, Inc. | P4 CAS 256657-23-5 |
| 4-(4-aminophenyl)butyric acid | 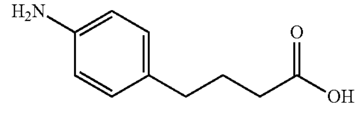 [SMILES: Nc1ccc(CCCC(=O)O)cc1] | Sigma-Aldrich | P5 CAS 15118-60-2 |
| 2-((4-aminophenyl)sulfonyl) acetic acid | 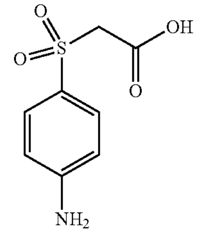 [SMILES: Nc1ccc(S(=O)(=O)CC(=O)O)cc1] | Shanghai ChemPartner Co., Ltd. | P6 |

TABLE 1-continued

| ligand | Structure | Vendor | Designation in figures |
|---|---|---|---|
| 2-((2-aminophenyl)thio) acetic acid | 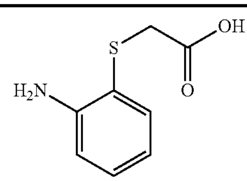 | Shanghai ChemPartner Co., Ltd. | P7 CAS 94-56-4 |
| 2-(2-(4-aminophenyl)acetamido) acetic acid | 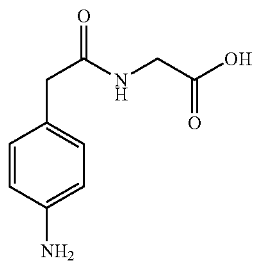 [SMILES: Nc1ccc(CC(=O)NCC(=O)O)cc1] | Shanghai ChemPartner Co., Ltd. | P8 |
| 2-(2-(4-aminobenzamido) acetamido)acetic acid | 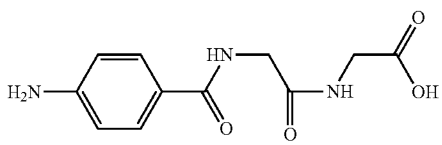 [SMILES: Nc1ccc(C(=O)NCC(=O)NCC(=O)O)cc1] | Synthesized | P9 |

A typical coupling protocol for attachment of the ligands is as follows. To 10 ml aldehyde resin was added 10 ml 0.05 M phosphate buffer (pH 7). Ligand, 4-(4-aminophenyl) butyric acid, 400 mg, was added to the suspension above in one portion. The pH of reaction mixture was measured and adjusted to 5.0-8.5 as needed. The reaction mixture was agitated at 37 degree C. for 0.5 hr. Sodium cyanoborohydride, 100 mg, was added to reaction mixture in one portion. The final reaction mixture was agitated at 37 degree C. for 3 hrs. The resin was collected on a frit and washed with 0.1N NaOH (2 bed volume) and di water (7 bed volume). Coupling of other ligands was substantially the same as described above.

Ligand density on the resin varied somewhat for different ligands as follows:

| Ligand | Ligand Density | Comment |
|---|---|---|
| 2-(4-aminobenzamido) ethanesulfonate | 102 μmol/ml | P1 |
| 4-aminophenylthioacetic acid | 86 μmol/ml | P2 |
| 4-aminophenylacetic acid | 92 μmol/ml | P3 |
| 2-aminohippuric acid | 88 μmol/ml | P4 |
| 4-(4-aminophenyl)butyric acid | 114 μmol/ml | P5 |
| 4-aminohippuric acid | 120 μmol/ml | |

Example 2

Solid support (UNOsphere) resins linked to Ligands P1, P2, P3, P4, or P5 (See Table 1 and FIG. 1) were tested for their ability to bind a set of commercially-available proteins (obtained from Sigma). The set of proteins was selected to cover a range of relevant protein properties (e.g. size, EP (electrostatic potential) and hydrophobicity).

The protocol used at pH 5.0 to screen the ligands coupled to UNOsphere was:

Column: 10 cm×0.5 cm ID
Flow Rate: 1 mL/min
Injection: 90 μL of 2 mg/mL protein solution dissolved in buffer A (0M NaCl)
Buffer A: 20 mM Acetate, pH 5.0
Buffer B: 20 mM Acetate, 1.5M NaCl, pH 5.0
Gradient: 1.5% B to 100% B over 45 CVs The results are shown in FIGS. 1-6. In the assay used, higher salt concentration for elution indicates stronger binding of the proteins to the ligand.

Example 3

Solid support (UNOsphere) resins linked to Ligands P6, P7, P8, or P9 (See Table 1) were tested for their ability to bind a set of commercially-available proteins (obtained from Sigma).

Ligand density on the resin varied somewhat for different ligands as follows:

| Ligand | Ligand Density | Comment |
|---|---|---|
| 2-((4-aminophenyl)sulfonyl) acetic acid | 60 μmol/ml | P6 |
| 2-((2-aminophenyl)thio) acetic acid | 70 μmol/ml | P7 |
| 2-(2-(4-aminophenyl)acetamido) acetic acid | 92 μmol/ml | P8 |
| 2-(2-(4-aminobenzamido)acetamido) acetic acid | 80 μmol/ml | P9 |

The protocol used at pH 6.0 to screen the ligands coupled to UNOsphere was:

Column: 10 cm×0.5 cm ID
Flow Rate: 1 mL/min
Injection: 90 μL of 2 mg/mL protein solution dissolved in buffer A (0M NaCl)
Buffer A: 20 mM Phosphate, pH 6.0
Buffer B: 20 mM Phosphate, 1.5M NaCl, pH 6.0
Gradient: 1.5% B to 100% B over 45 CVs The results are shown in FIGS. 7-12. In the assay used, higher salt concentration for elution indicates stronger binding of the proteins to the ligand.

Figure 7:
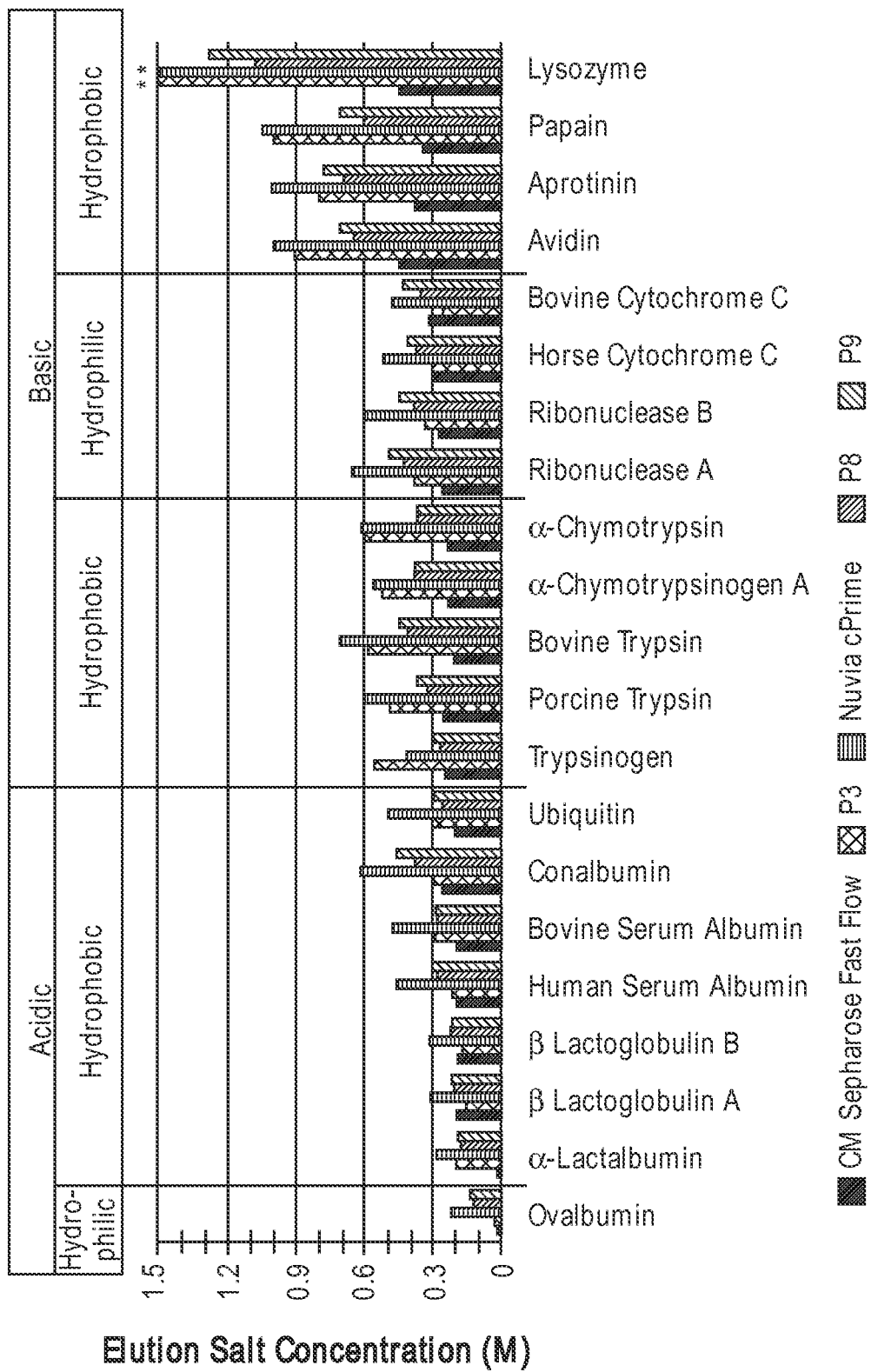
Figure 8:
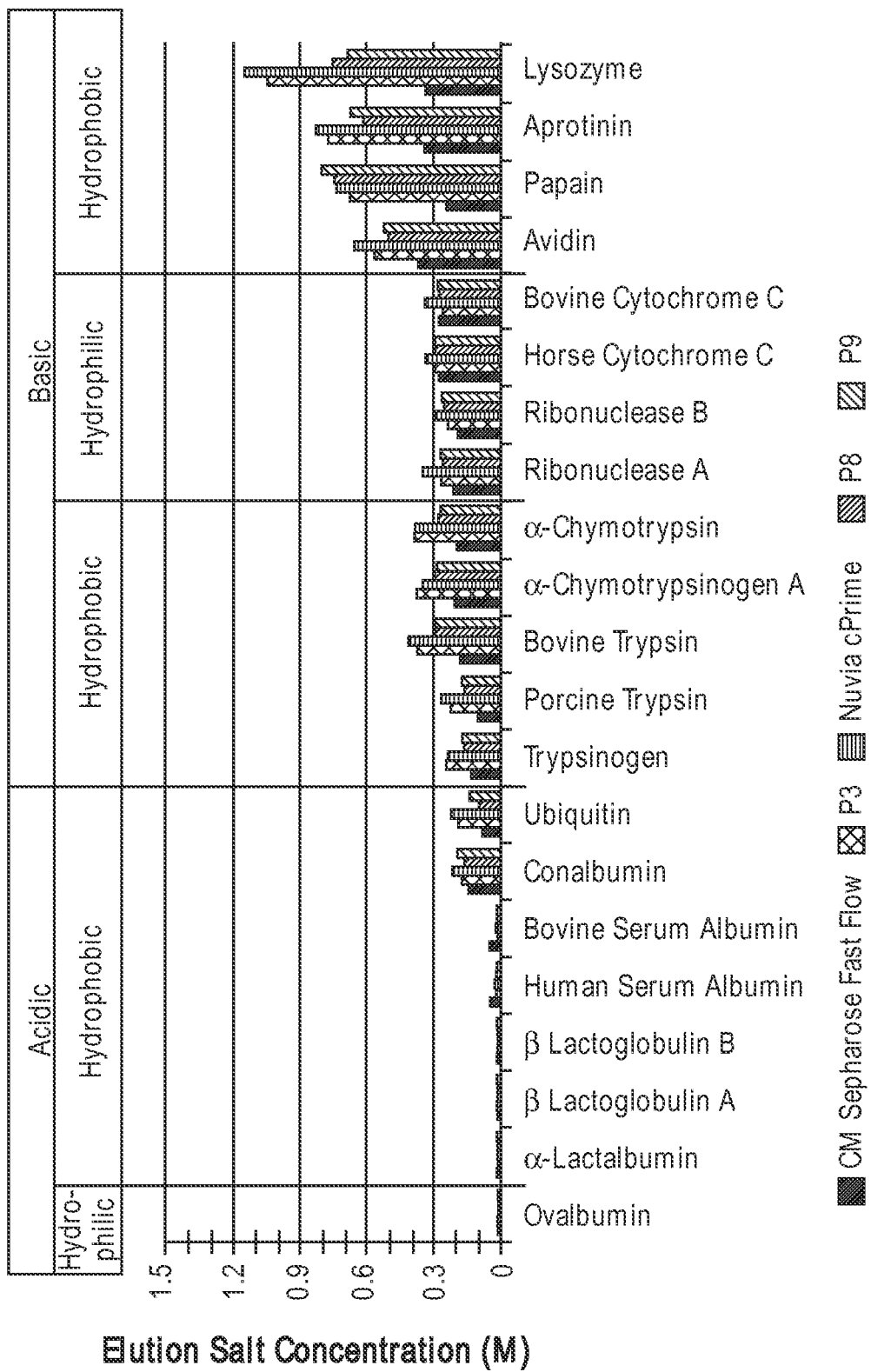

P8 and P9 results at pH 5 are summarized in FIG. 7; these prototypes behave similarly as mixed mode media but have weaker binding, compared to cPrime. P8 and P9 results at pH 6 are summarized in FIG. 8.

Figure 9:
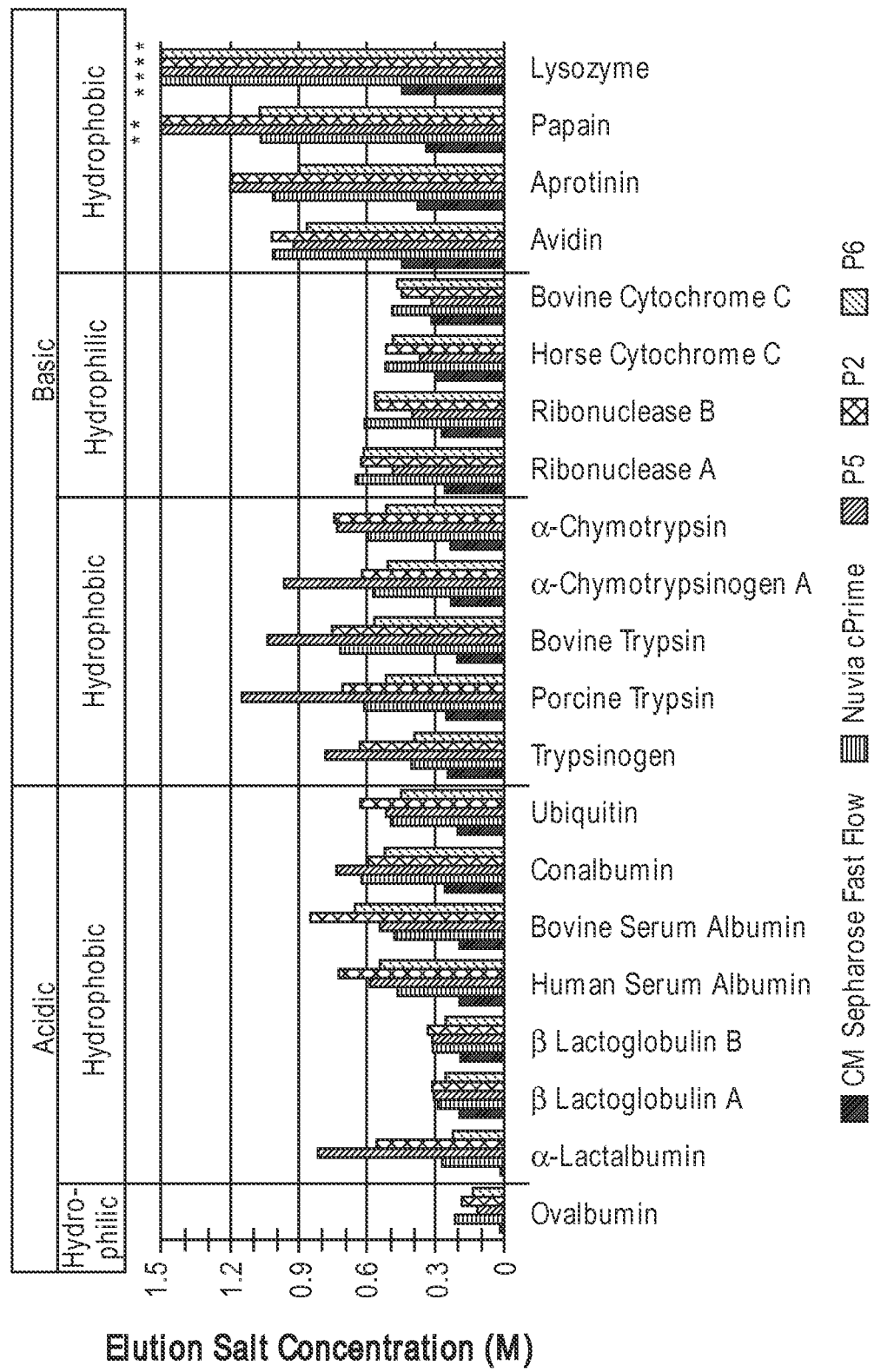
Figure 10:
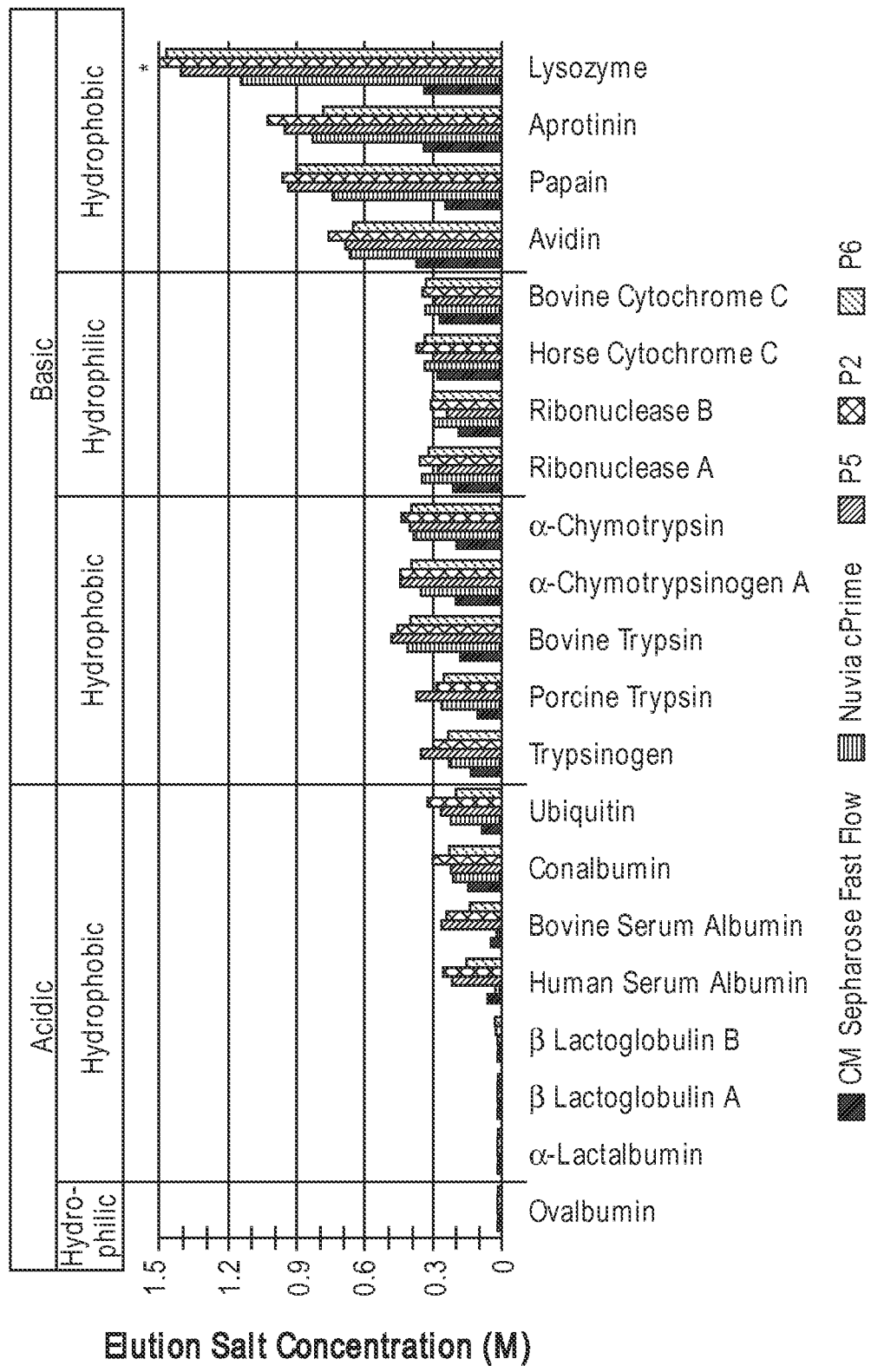

P6 results at pH 5 are summarized in FIG. 9. The sulfone behaves similarly as a mixed mode, but with slightly weaker binding (except for lysozyme). Asteric's above the bar indicate the protein did not elute at the end of the salt gradient. P6 results at pH 6 are summarized in FIG. 10.

Figure 11:
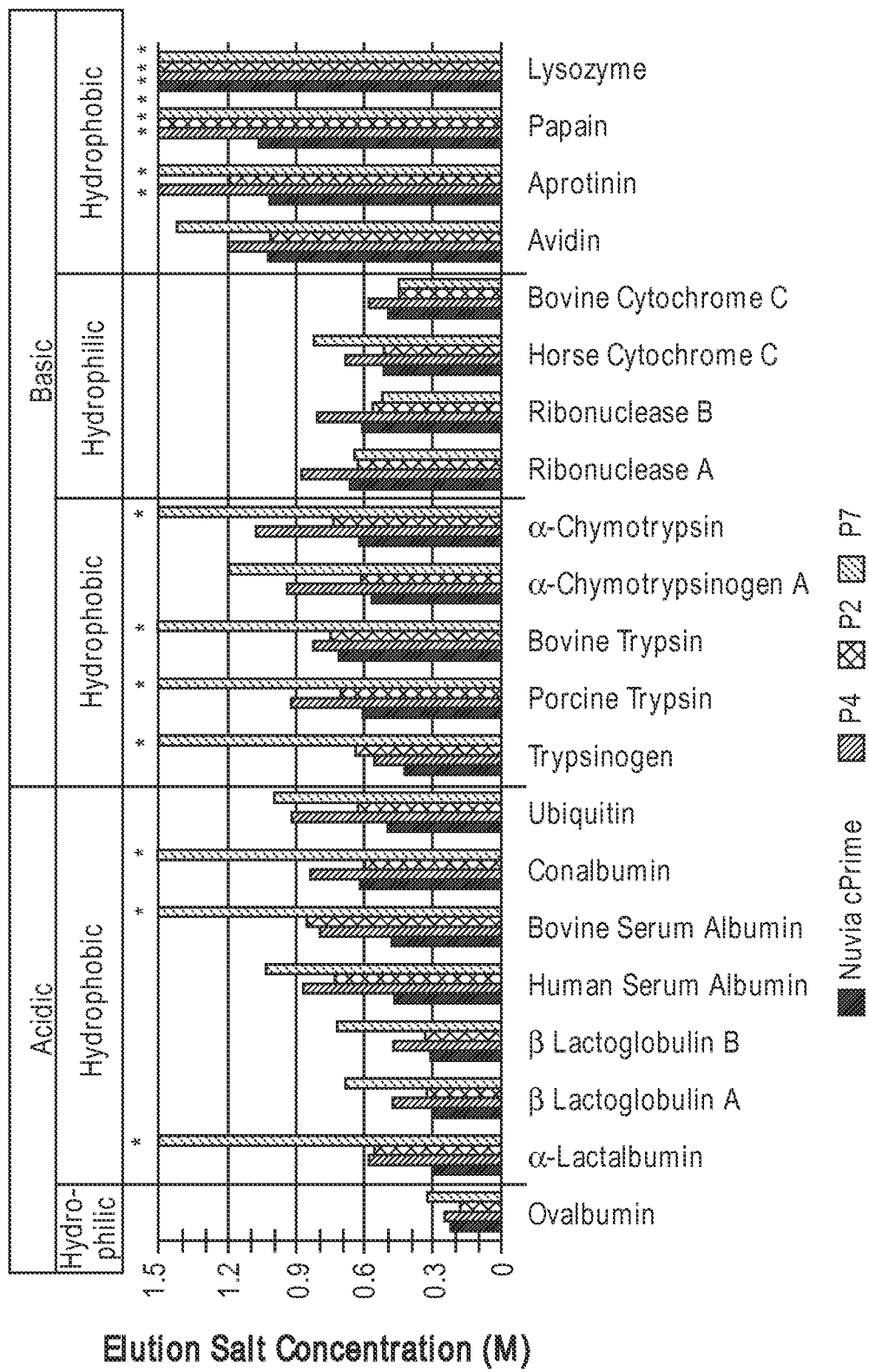
Figure 12:
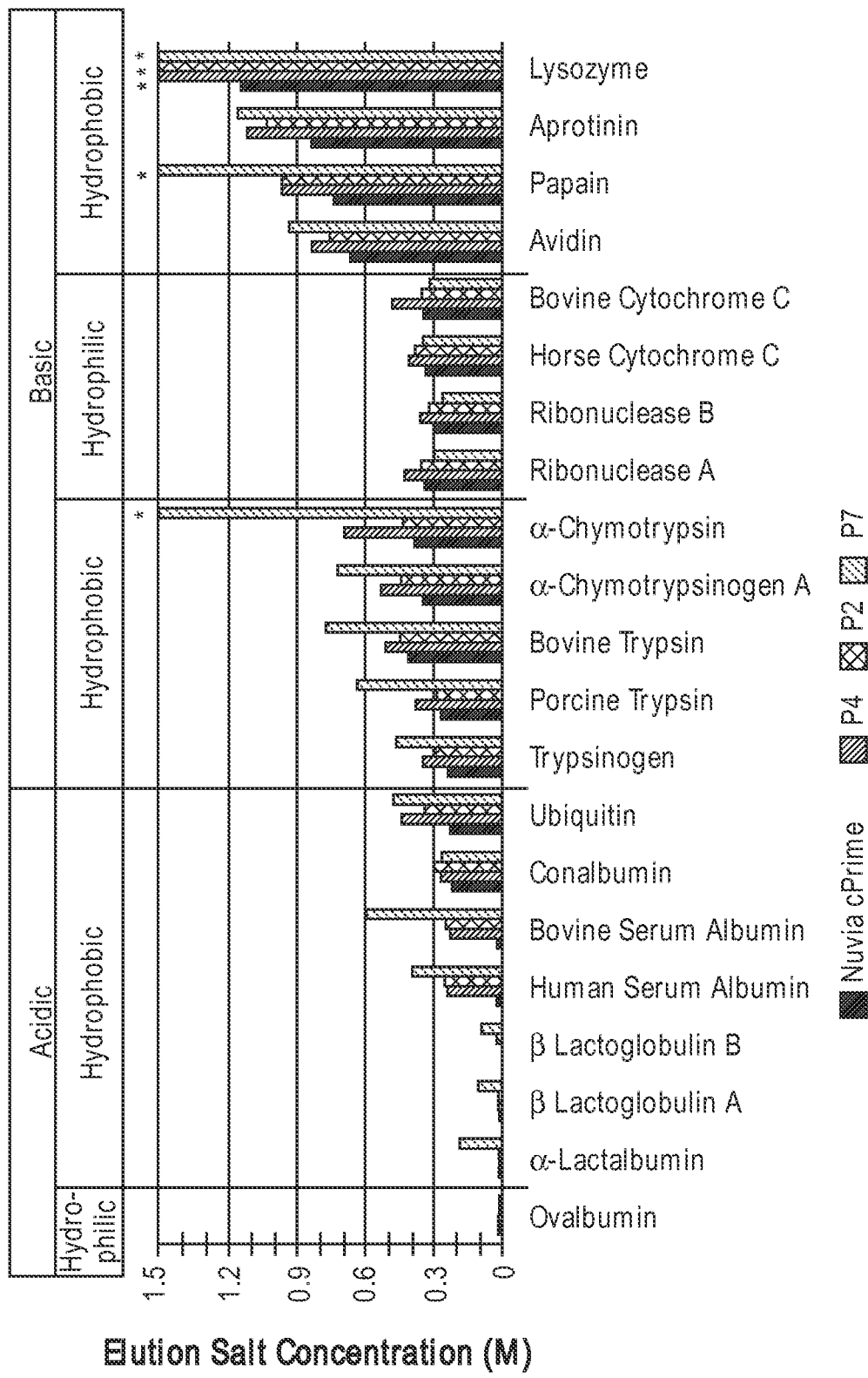

P7 results at pH 5 are summarized in FIG. 11. P7, with ortho-linked aminophenylthioacetic acid and enhanced solvent exposure of the aromatic group, provides stronger retention of more hydrophobic proteins compared with cPrime, P4 (ortho-linked aminohippuric acid) or P2 (para-aminophenylthioacetic acid). P7 results at pH 6 are summarized in FIG. 12.

Example 4

Ligand P9 was synthesized as follows. A 10% solution of 2-(2-(4-nitrobenzamido)acetamido)acetic acid in DMSO was treated with 1 equivalent of HCl, and then it was reduced by hydrogen (in a balloon) and catalyst 10% Pd/C. The reaction progress was monitored by MS and more hydrogen (in a balloon) and catalyst 10% Pd/C were introduced as needed. After all 2-(2-(4-nitrobenzamido)acetamido)acetic acid was reduced, the reaction mixture was filtered. The product, 2-(2-(4-aminobenzamido)acetamido) acetic acid (MS, M+H, predicted, 252.09, actual, 252.09), in the resulting solution was coupled directly onto the resin as described herein.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

What is claimed is:

1. A mixed-mode chromatography medium comprising a ligand coupled to a solid support, said ligand is:

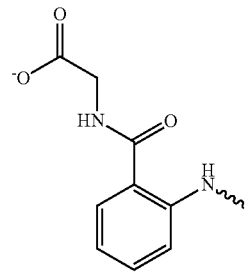

wherein the curving line indicates where the ligand is directly coupled to the solid support without a spacer through an amine on the benzyl ring attached at the ortho position, wherein the solid support comprises a copolymer of 3-allyloxy-1,2-propanediol and vinyl pyrrolidinone; wherein the mixed-mode chromatography medium is in contact with a source solution maintained at a pH of 4.0 to 6.0 such that a target protein from the source solution binds to the ligand.

2. The mixed-mode chromatography medium of claim 1, wherein said solid support has pores of a median diameter of 0.5 micron or greater with substantially no pores of 0.1 micron or less in diameter.

3. The mixed-mode chromatography medium of claim 1, wherein said solid support is a membrane.

4. The composition of claim 1, wherein the source solution is at pH 5.

5. The composition of claim 1, wherein the target protein is an antibody, enzyme, clotting factor, transcription factor, growth regulator or phosphoprotein.

6. The composition of claim 1, wherein the target protein is selected from the group consisting of lysozyme, papain, aprotinin, avidin, bovine trypsin, ribonuclease A, ribonuclease B, trypsinogen, α-chymotrypsin, ubiquitin, porcine trypsin, conalbumin, Horse Cytochrome C, α-chymotrypsinogen A, bovine serum albumin, human serum albumin, β-lactoglobulin B, β-lactoglobulin A, α-lactalbumin A and ovalbumin.

7. The chromatography composition of claim 1, wherein the source solution comprises sodium chloride.

* * * * *